(12) United States Patent
Keizer et al.

(10) Patent No.: US 7,618,829 B2
(45) Date of Patent: Nov. 17, 2009

(54) METHOD OF DETECTING MULTIPLE ANALYTES

(75) Inventors: Gerrit Dirk Keizer, Harderwijk (NL); Wilhelmus Joseph Gerardus Schielen, Levstad (NL)

(73) Assignee: Prionics Lelystad, B.V., Lelystad (NL)

( * ) Notice: Subject to any disclaimer, the term of this patent is extended or adjusted under 35 U.S.C. 154(b) by 87 days.

(21) Appl. No.: 10/568,633

(22) PCT Filed: Sep. 3, 2004

(86) PCT No.: PCT/NL2004/000615

§ 371 (c)(1),
(2), (4) Date: Oct. 26, 2006

(87) PCT Pub. No.: WO2005/021130

PCT Pub. Date: Mar. 10, 2005

(65) Prior Publication Data

US 2007/0065811 A1  Mar. 22, 2007

(30) Foreign Application Priority Data

Sep. 3, 2003  (EP)  .................................. 03077782

(51) Int. Cl.
*G01N 33/543* (2006.01)
*G01N 33/545* (2006.01)

(52) U.S. Cl. ...................... 436/518; 422/58; 435/287.2; 435/288.3; 435/288.4; 436/524; 436/527; 436/531; 436/809

(58) Field of Classification Search ........................ None
See application file for complete search history.

(56) References Cited

U.S. PATENT DOCUMENTS

| 4,077,845 A | * | 3/1978 | Johnson | 435/33 |
| 4,111,754 A | * | 9/1978 | Park | 435/288.5 |
| 4,294,931 A | * | 10/1981 | Levin et al. | 435/288.5 |

(Continued)

OTHER PUBLICATIONS

Aranha-Creado, H., et al. "Clearance of Murine Leukaemia Virus from Monoclonal Antibody Solutions by a Hydrophilic PVDF Microporous Membrane Filter." *Biologicals* vol. 26, No. 2 (1998) pp. 167-172.

(Continued)

*Primary Examiner*—Christopher L Chin
(74) *Attorney, Agent, or Firm*—Ladas & Parry LLP (57) ABSTRACT

The invention relates to a a microtiter plate and its use in a method of the invention, which microtiter plate comprises a plurality of containers, wherein the bottom of each container comprises a (semi-)permeable membrane capable of directly or indirectly binding an analyte, and wherein each container is separated from an adjacent container by a container dividing wall, wherein the containers are grouped in one or more clusters, each cluster comprising at least two containers, wherein said clusters are separated from adjacent clusters by a cluster dividing wall and wherein at least part of the container dividing wall is lower than the cluster dividing wall or wherein the container dividing wall contains at least one passageway connecting at least two adjacent containers within a cluster, said passageway being at a distance from the bottom of the container and at least partly below the top of the container.

16 Claims, 2 Drawing Sheets

U.S. PATENT DOCUMENTS

| | | | | |
|---|---|---|---|---|
| 4,545,958 | A | * | 10/1985 | Dopatka ................... 422/102 |
| 4,895,706 | A | * | 1/1990 | Root et al. ................. 422/102 |
| 4,948,442 | A | * | 8/1990 | Manns ..................... 156/73.1 |
| 4,948,564 | A | * | 8/1990 | Root et al. ................. 422/101 |
| 5,108,704 | A | * | 4/1992 | Bowers et al. .............. 422/70 |
| 5,110,556 | A | * | 5/1992 | Lyman et al. .............. 422/101 |
| 5,227,290 | A | * | 7/1993 | Pocock ..................... 435/7.1 |
| 5,279,937 | A | | 1/1994 | Rowe |
| 5,326,533 | A | * | 7/1994 | Lee et al. ................... 422/101 |
| 5,417,923 | A | * | 5/1995 | Bojanic et al. ............. 422/101 |
| 5,441,894 | A | * | 8/1995 | Coleman et al. ........... 436/518 |
| 5,948,363 | A | * | 9/1999 | Gaillard .................... 422/102 |
| 6,315,940 | B1 | * | 11/2001 | Nisch et al. .............. 435/287.1 |
| 6,803,239 | B2 | * | 10/2004 | Bunn et al. ................ 436/518 |
| 2002/0164812 | A1 | * | 11/2002 | DeLucas ................... 436/86 |
| 2003/0113713 | A1 | | 6/2003 | Glezer et al. |

OTHER PUBLICATIONS

Winklhofer, K.F. et al. "A Sensitive Filter Retention Assay for the Dectection of PrP$^{Sc}$ and the Screening of Anti-Prion Compounds" *FEBS Letters* (2001) vol. 503, pp. 41-45.

Guerin-Marchand, C. et al. "DMISA (Dissociated Membrance Immunosorbent Assay), a New ELISA Technique Performed with Blotted Samples" *Journal of Immunological Methods* (1994) vol. 167, pp. 219-225, XP-002272172.

Stya, M. et al. "Dot-Based ELISA and RIA: Two Rapid Assays that Screen Hybridoma Supernatants Against Whole Live Cells" *Journal of Immunological Methods* (1984) vol. 73, pp. 75-81, XP-002272173.

Barnett, G.R. et al. "An Improved Membrane-Filtration Enzyme Immunoassay for the Rapid Serological Diagnosis of Viral Infections" *Journal of Virological Methods* (1988) vol. 20, pp. 323-332, XP-002272171.

* cited by examiner

Figure 1

Figure 2

METHOD OF DETECTING MULTIPLE ANALYTES

The invention relates to a rapid and cost-effective method for the detection of analytes in a sample. In particular, the present invention relates to a microtiter plate, the bottom of which comprises a (semi-)permeable membrane filter and to the use thereof in a method for the simultaneous detection of multiple analytes in a sample fluid.

The use of Enzyme-Linked Immunosorbent Assay (ELISA) for the detection and quantification of specific analytes, such as antibodies or antigens, is a well standardized diagnostic methodology. At present such methods are routinely performed using polystyrene microtiter plates of 96 wells. The method comprises a number of critical steps including i) the immobilization of a capture ligand to the walls of the microtiter plate well (the so-called coating step), ii) the separation of bound and free capture ligand by washings, iii) the binding of an analyte of interest to the bound capture ligand, iv) the separation of bound and free analyte by washings, v) the binding of a conjugated enzyme to the bound analyte, vi) the separation of bound and free conjugate by washings, and vii) the detection of bound conjugate by the enzymatic conversion of an added substrate. Due to these essential process steps, and particularly the extensive washing procedures that are necessary to separate bound from unbound reactants, the method is laborious and relatively slow.

Apart from the fact that diffusion processes are involved in the various binding reactions, thus retarding the procedure, the large number of washing steps creates large amounts of waste fluids. This is particularly problematic when using biohazard materials or infectious samples and creates large amounts of contaminated waste fluids.

Furthermore, in order to perform tests on multiple analytes present in one sample, separate microtiter plates must be coated with distinct capture ligands, capable of specifically binding the individual analytes to be determined. Thus, one sample must be applied to different plates. Separate plates are also sometimes required because coating differs from capture ligand to capture ligand (e.g. different buffers, incubation times, incubation temperatures, etc.). In addition separate plates are required since coating of individual wells on one plate with distinct capture ligands harbours the risk of cross-contamination between wells.

In many diagnostic fields, an individual sample is tested for the presence or absence of a number of analytes. When detecting a large number of different analytes in samples by ELISA, the above described requirement for separate microtiter plates for each individual ELISA test holds several disadvantages. For instance, a large number of wells of a microtiter plate may remain unused in cases that only a limited number of samples is tested. Also, the test samples must be aliquoted over different test plates in case that different analytes are to be determined therein, thus necessitating relatively large sample volumes. Furthermore, results of different plates are inherently difficult to compare. As stated above, another problem of the methods of the prior art is that large volumes of washing fluids are required and that in case of detecting infectious agents, large amounts of contaminated waste fluids arise. When processed sequentially the procedure is very time-consuming and prone to error.

The present inventors have now found a method for detecting an analyte in a liquid sample that overcomes one or more disadvantages of the methods of the prior art. The method involves a) the provision of a specific microtiter plate comprising a plurality of containers, wherein the bottom of each container comprises a (semi-)permeable membrane filter capable of directly or indirectly binding an analyte, and wherein each container is separated from an adjacent container by a container dividing wall, wherein the containers are grouped in one or more clusters, each cluster comprising at least two containers, wherein said clusters are separated from adjacent clusters by a cluster dividing wall and wherein at least part of the container dividing wall is lower than the cluster dividing wall or wherein the container dividing wall contains at least one passageway connecting at least two adjacent containers within a cluster, said passageway being at a distance from the bottom of the container and at least partly below the top of the container. The method of the invention further comprises the steps of b) applying said liquid sample to at least one cluster of containers, filtering said sample through said membrane filter, thereby binding said one or more analytes to said membrane filter or capture ligand, and optionally performing washing steps; and c) detecting said bound one or more analytes in said containers by performing a binding assay on said membrane filter, said binding assay preferably being a chemiluminescent immunoassay.

The invention further relates to the specific microtiter plate itself as provided in the above method and to the use thereof in the detection of analytes.

In fact, when using the above method, the present inventors have found that this procedure greatly reduces the required amount of washing fluids. Moreover, it was found that different analytical tests may be performed on a single microtiter plate.

As a result thereof, the present inventors have found that one sample may be applied to a number of adjacent containers on a single microtiter plate by a single application step in order to perform different analytical tests thereon.

In a first aspect, the present invention provides a method for detecting an analyte in a sample as set out herein above. In embodiments of the method of the invention, a plurality of sample containers is provided in the form a microtiter plate. The entire bottom of said microtiter plate being provided with a (semi-)permeable membrane filter, so that the bottom of each container is comprised of a (semi-)permeable membrane filter.

As used herein, the terms "(semi-)permeable membrane filter", "(semi-)permeable membrane" and "membrane filter" are all interchangeable.

The plurality of containers can be of any number and shape and can be arranged in any ornamental pattern, preferably, the plurality of containers is provided in the format of a standard 96-well microtiter plate, but also formats comprising about 384, 864, 1536, 2400 or about 3456 wells may be particularly suitable.

The number of adjacent containers in a cluster of containers may be any number suitable for the purpose of determining multiple analytes in plurality of containers. In a particularly preferred embodiment of the above method, the method involves the use of a microtiter plate comprising at least $n^2$ adjacent containers, wherein n is an integer, preferably an integer from 2-10, more preferably 2-5. Such numbers are advantageous for coding of positions, standardization of procedures and for manufacturing reasons.

The present invention also relates to a microtiter plate comprising a plurality of containers, wherein the bottom of each container comprises a (semi-)permeable membrane capable of directly or indirectly binding an analyte, and wherein each container is separated from an adjacent container by a container dividing wall, wherein the containers are grouped in one or more clusters, each cluster comprising at least two containers, wherein said clusters are separated from adjacent clusters by a cluster dividing wall and wherein at least part of the container dividing wall is lower than the cluster dividing wall or wherein the container dividing wall contains at least one passageway connecting at least two adjacent containers within a cluster, said passageway being at a distance from the bottom of the container and at least partly below the top of the container.

In this method, the workings of said microtiter plate is such that when a sample fluid is applied to a first container in a cluster, and the amount of said applied fluid is such that the fluid level rises above the container dividing wall or above the position of the passageway, at least a portion of said applied sample fluid will flow or spill from said first container into an adjacent second container until the fluid level is again even with the container dividing wall or below the position of the passageway. Now when an amount of fluid is applied that is, due to its volume, capable of dividing evenly over all containers within a cluster, then all said containers within that cluster may be provided with an equal volume of sample fluid in a single sample application step.

Preferably, the container dividing walls have a particular minimal height or the position of the passageway between adjacent and connected containers is elevated above the bottom of the container that an amount of sample fluid can be contained therein. Essentially said amount is sufficient for the performing the detection assay on the analyte. A typical dimension of a container is one that is capable of containing, or has a capacity before spill-over, of between 1 and 5000 µl, preferably from 5 to 1000 µl, more preferably between 5 and 250 µl of fluid. Thus, the microtiter plate of the present invention is characterised in the presence of cluster-dividing walls and container-dividing walls, wherein the cluster dividing walls allow for spill-over of sample fluid from one container to another. Essentially in a method of the invention, spill-over will occur when the amount of fluid loaded into a container exceeds the capacity before spill-over, also termed herein the spill-over volume. The height of a container-dividing wall is typically 0.1 to 20 millimeters, preferably 1 to 5 millimeters. The height of a cluster-dividing wall is typically 0.1 to 15 millimeters higher than the container-dividing wall, preferably 1 to 5 millimeters higher.

The container dividing and cluster dividing walls may be of any material and may for instance be all clear, white, black or transparent or light-blocking and may in principle be of any color. Preferably, the walls are light-blocking.

A method according to the present invention may in principle be performed for detecting analytes in any liquid sample an in any fluid, such as cell culture supernatants, water (including potable, cooling tower, waste and process water), extracts of soil or other fluids such as oil, but preferably body fluids such as, for example, milk, colostrums, urine, (whole) blood, serum, plasma, pleural fluid, gastric fluid, duodenal fluid, intraocular fluid, ascitic fluid, peritoneal fluid, amniotic fluid, synovial fluid, cystic fluid, cerebrospinal fluid, vaginal fluids (including menstrual fluids), semen, sputum, saliva, extracts of faeces or manure, sweat or exudate from lesions.

For the detection of analytes in non-fluidic samples, such as biopsy tissue samples, a sample may suitably be prepared in the form of a slurry, a suspension, a solution, a macerate, a homogenate, and the like. The sample may thus comprise a fluid sample, a fluid from a sample, a fluidised sample or a preparation from a sample that is fluidic. The analyte may be present in the sample either in suspended or dissolved form.

The sample may be derived from any source or any subject including, but is not limited to, mammals, including, e.g., a human, non-human primate, mouse, pig, cow, goat, cat, rabbit, rat, guinea pig, hamster, horse, monkey, sheep, or other non-human mammal; and non-mammal animals, including, e.g., a non-mammalian vertebrate, such as a bird (e.g., a chicken or duck) or a fish, and a non-mammalian invertebrate.

The method is useful for detecting a large variety of analytes in a sample. Analytes such as nucleotides, peptides or saccharides, or polymers thereof, such as DNA or RNA, proteins and polysaccharides, may all be detected by using a method of the present invention. Also, antibodies, antigens, enzymes, cofactors, metabolites, hormones, prions, viruses, bacteria and/or fungi may be detected. In general any chemical or biological substance for which a specific binding partner can be provided, such as, for instance, each of the binding partners in an antibody-antigen pair of binding partners, or binding pairs such as enzyme/substrate, charge-transfer complexes, stacking-complexes, covalent complexes, etc., can be determined by using the present method.

The term "more" in "one or more analytes" as used herein, is understood to indicate different types of analytes.

As used herein, the terms "antibody" and "antibodies" refer to monoclonal antibodies, multispecific antibodies, synthetic antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies of the invention), and epitope-binding fragments of any of the above. In particular, antibodies of the present invention include immunoglobulin molecules and immunologically active portions of immunoglobulin molecules, i.e., molecules that contain an antigen binding site that immunospecifically binds to an analyte to be detected. The immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule.

The methods and microtiter plates of the present invention are particularly useful for detecting multiple analytes in a biological sample such as for instance various infectious disease agents or an antibody there against in man or animals or in general parameters in test panels or menus of tests for the operating room, emergency testing, fertility testing, feed-conversion, tumor markers, auto-immune diseases, bone-and-mineral diseases, metabolic diseases, gastro-intestinal disorders and parameters, hemostasis, drugs of abuse, diabetes, ketosis, leucosis, the blood donation field as well as test panels for hormones, allergens, GMO's, and contaminants and/or residues in food, feed or the environment.

Preferred analytes to be detected by such a multiple analyte assay are viruses and bacteria or antibodies there against. In a particularly preferred embodiment, agents (or antibodies there against) causing such diseases as bovine spongiform encephalopathy (BSE), foot and mouth disease, bovine respiratory syncytial virus (BRSV) induced disease, bovine viral diarrhoea, brucellosis, leptospirosis, lungworm infection, classical swine fever, porcine parvo virus (PPV) induced disease, pseudorabies virus (PrV) induced disease (or Aujeszky's disease), swine vesicular disease, anthrax, Salmonellosis, Campylobacter induced disease, E. coli induced disease, cholera, and other bacterial induced diseases, HIV, HBV, HCV, HTLVI and/or HTLVII are detected by using a method of the invention.

Also menus of tests for hormones, metabolic diseases, feed-conversion, fertility, bone-and-mineral disease, ketosis, leukosis, etc. may be prepared, wherein said menu comprises of a number of tests for different agents. Particularly suitable menus are those aimed at tests performed in a specific field, such as in the food/feed industry, which menu may then comprise microbiological tests on food safety, tests for the presence of genetically modified organisms (GMO's), or the presence of contaminants, toxins, residues and hormones in food and or feed products.

Other suitable menus are those aimed at tests performed in the field of environmental detection such as panels for the detection of atrazines, pyretroiden, agricultural toxins or pesticides such as herbicides, fungicides, molluscicides, insecticides, etc. The skilled person will easily identify other suitable menus for other fields of testing. For example, panels of assays may be developed for measuring in a multiple analyte assay a plurality of analytes or activities associated with a particular biological system (e.g., panels of immunoassays or hybridization assays for monitoring cytokine mRNA or protein levels), disease state (e.g., panels of assays for cardiac markers, for identifying allergens responsible for allergic reactions, for identifying infectious organisms, etc.), tissue type, organism, class of protein, enzyme or biological molecule, etc. In one embodiment, a panel of assays is used to provide a fingerprint for identifying a biological system (e.g., a pattern of analyte levels associated with a particular cell type, organelle type, organism type, tissue type, bacteria or virus). For example, a plurality of assays for different components found within a genus of biological systems can be used to identify species or subspecies within that genus. In another embodiment, a differential measurement involving a plurality of assays for different components within a biological system is used to identify the state of the biological system (e.g., diseased vs. normal state, activated vs. normal state, etc.) or to identify the components within a biological system that are affected by an external condition or stimulus (e.g., changes in the distribution of components associated with development of a disease state, addition of a stimulatory species, addition of a potential drug candidate, changes in environmental conditions such as pH, temperature, etc.). Assay panels may also be used to determine the function of one or more proteins. For example, a protein may be screened against a patterned library of enzyme substrates and/or potential binding partners to identify enzymatic or binding activities. Conversely, a patterned library of proteins may be exposed to a known biological material to determine if any of the proteins binds to, reacts with or is otherwise transformed by the biological material.

A preferred analyte that is detected by a method of the invention is the causative agent of transmissible spongiform encephalopathy (TSE) such as scrapie (Sc), BSE, chronic wasting disease (CWD) and Creutzfeldt-Jakob disease (CJD), and in particularly those caused by prions $PrP^{Sc}$, $PrP^{BSE}$, $PrP^{CWD}$, $PrP^{CJD}$.

As used herein a container is defined as a (circular) cylindrical container comprising an open top end, walls and a closed a bottom end. A typical container is a well of a regular microtiter plate. According to the present invention the bottom of the container is provided with a (semi-)permeable membrane filter. Herein, the (semi-)permeable membrane filter represents the bottom of the container and fluid applied to the container may be removed from that container by providing a reduced gas pressure or vacuum under said membrane filter, thereby drawing the liquid contents of the container through said filter. Alternatively, the fluid applied to the container may suitably be removed from that container by providing a positive gas pressure, thereby pushing the liquid contents of the container through said filter. The actual shape of the container is not essential as long as suitable means such as for instance a vacuum aspirator can be effectively used for removing its contents through the membrane filter comprised in the bottom of said container. In a preferred embodiment of a microtiter plate of the invention the plate is specifically adapted to be used in combination with a vacuum aspirator.

The container may be of any suitable rigid material such as glass, polystyrene, polyacryl, polyamide, polyethylene, polypropylene, acrylate butadiene styrene (ABS), Barnox, PVC, nylon, EVA, PET, etc and combinations thereof. The material may for instance be all clear, white, black or transparent or light-blocking and may in principle be of any color.

The (semi-)permeable membrane filter may be of any suitable material such as cellulose nitrate, cellulose acetate, mixed cellulose ester, polysulfone, poly-ether sulfone, polypropylene, polyvinylidene fluoride (PVDF), polycarbonate, nylon, glass (e.g. as microfibres), or polytetrafluoroethylene (PFTE or Teflon®). In principle the filter may be hydrophilic or hydrophobic, positively of negatively charged, depending on the specific application and the analyte tested or ligands used. Polyvinylidene fluoride (PVDF) is a particularly preferred membrane filter in the case of detecting prions.

The (semi-)permeable membrane filter should be capable of binding analytes and/or capture ligands for analytes while allowing for the passage of non-reacted reagents, such as unbound capture ligands and/or unbound analytes in washing fluids. In principle therefore, all reagents except for the analyte to be detected and the capture ligand used in a method of the invention, should be capable of unhindered passage of the (semi-)permeable membrane so that they may be washed away.

Advantageously, the (semi-)permeable membrane has a nominal pore size in the range of about 0.01 to about 15 μm, preferably of about 0.02 to about 2 μm, even more preferably about 0.05 to about 0.45 μm.

According to the invention the membrane filter is capable of binding the analyte of interest. This binding may either be a direct binding such as, for instance, a binding wherein the analyte binds to the membrane filter by electrostatic interaction, or by hydrophobic interaction, covalent binding, charge-transfer-interactions, etc. Such direct binding may be a permanent or irreversible binding such as covalent binding, or a reversible binding.

Alternatively, the binding of the analyte of interest to the membrane filter may be indirect, i.e., facilitated by providing a specific or non-specific binding partner for the analyte in the form of a capture ligand on or within said membrane filter, preferably in the form of a membrane coating. The capture ligand is then immobilized on or within said membrane filter, and any suitable technique known to the skilled person may be employed for such immobilization. Suitable capture ligands may be any binding partner capable of binding to the analyte, such as, for instance, (strept)avidine or antibodies, preferably monoclonal antibodies, that may be raised against specific analytes and that can then be used to bind the analyte indirectly to the membrane filter. Other suitable capture ligands constitute, for instance, complementary nucleic acids, including DNA, PNA or RNA probes or the like. The skilled person is aware of the various binding partners that can be used as capture ligands in a method of the present invention.

The binding to the (semi-)permeable membrane is preferably specific. Indirect binding as described above has the advantage that the binding thereof is in most cases specific, in particular when using specific binding partners for the analyte as capture ligands.

Instead of the laborious and time-consuming coating procedures of the prior art, the present method involves the application of the capture ligand in a suitable liquid medium, applying the liquid medium comprising the capture ligand to the container, optionally incubating for a short period, usually several minutes, and filtering the entire contents of the container trough the membrane filter, preferably by vacuum pressure thereby effecting the binding of the capture ligand to the (semi-)permeable membrane. Optionally, a small amount of a suitable washing solution may then follow to clean the membrane filter of unbound capture ligand. Such a procedure is much faster than the conventional coating procedures.

There is also the possibility to first bind a capture ligand to the analyte, for instance by providing such a capture ligand to the sample, thereby creating a capture ligand-analyte complex, and binding said complex to the membrane filter, thereby also establishing an indirect binding of the analyte to the membrane filter.

A method for detecting an analyte in a sample according to the present invention comprises a second step of applying said liquid sample to said one or more sample containers, filtering said sample through said membrane filter, preferably by vacuum pressure, thereby binding said one or more analytes to said membrane filter, and optionally performing washing steps.

As stated above, the binding of said one or more analytes to the membrane filter may either be directly or indirectly. In both cases, a specific medium or buffer may be required to optimize binding of the analyte to the membrane filter directly, to facilitate the interaction between the analyte and the membrane filter-immobilized capture ligand or to optimize the binding of the analyte-capture ligand complex to the membrane filter.

In performing the detection method of the invention it may for instance be desirable to include certain "blockers" in the incubation medium to assure that non-specific proteins or proteases present in the experimental sample do not cross-link or destroy capture ligands, such as for instance antibodies, to yield false positive or false negative results. The selection of "blockers" therefore may add substantially to the specificity of the assay methods described in the present invention. The skilled person will be aware of the various components that may be used in such media or buffers to enable and optimize binding of said analyte either to the membrane filter directly, or to a capture ligand, such as an antibody.

A third step in a method for detecting one or more analytes in a sample according to the present invention comprises detecting said bound one or more analytes in said sample containers by performing a binding assay on said membrane filter. The skilled person is well aware of the various possibilities of detecting the immobilized analyte on the membrane filter by using binding assays. Very suitable assays thereto are immunoassays, such as ELISA assays.

Typically, binding assays comprise a binding phase, wherein a specific binding partner binds to the analyte, and a subsequent detection phase, wherein a signal is measured. The binding phase may be performed prior to applying said liquid sample to said one or more sample containers, i.e. by adding a binding partner to a sample fluid, and allowing it to bind to the analyte prior to performing the second step of the method of the invention. The binding phase is preferably performed in the third step. The detection phase on the other hand is always performed on the membrane filter in the third step of a method of the present invention.

In principle, any type of detection method is suitable for use in a method of the present invention. For instance, chromogenic, phosphorescent, luminescent and fluorescent methods are all suitable for use in a method for detecting one or more analytes in a sample according to the present invention. Luminescence techniques may comprise bioluminescence, electrochemiluminescence and chemiluminescence. Of the latter, both glow type, by using for instance HRP or AP for enzymatic conversion of substrates, and flash type, by activation of luminol, dioxethane or acridinium-ester label, are suitable. The type of detection method used will depend on the assay-conditions, and the person skilled in the art will be able to select a suitable method. Chemiluminescence is preferred over electrochemiluminescence since this allows for simpler testing as no electrode is required to apply an electrical charge to the site of analysis (i.e. the container or (semi-)permeable membrane surface to be measured) and requires no specific detection equipment. Moreover whereas equipment that is brought into contact with infectious material may be intensely cleaned, equipment that is brought into contact with prion-related material can never be used again and must be destroyed. Therefore, a microtiter plate according to the present invention is preferably cheap and consumable.

A typical chemiluminescent immunoassay for the detection of the application immobilized analyte either directly bound or via a specific capture ligand on the membrane filter includes i) the application of an enzyme-antibody conjugate, capable of specific binding to the analyte in a suitable conjugation buffer; ii) a short incubation to allow specific binding to occur, usually in the order of 30 minutes to 2 hours, depending incubation conditions; iii) the removal of the unbound conjugate by filtering the entire contents of the container through the membrane filter, preferably by vacuum pressure; iv) optional washing of the membrane filter by a washing solution; v) application of the chemiluminescent substrate and vi) luminometric evaluation of the chemiluminescence produced in the container. For chemiluminescent applications, the container is preferably of a white coloured material, while for fluorescent applications a black coloured material is preferred.

The method of the invention may thus comprise the use of a first binding partner as a capture ligand in a step of binding the analyte to the membrane filter and the use of a second binding partner as part of the detection assay. Such an embodiment is known in the art as a sandwich type assay.

In a preferred embodiment of the method of the invention, the sample containers are provided in the form of a microtiter plate comprising a plurality of sample containers, said microtiter plate then being used for performing a method of the invention. The entire bottom of said microtiter plate is then provided with a (semi-)permeable membrane filter that is sealably connected to the walls of each container, so that the bottom of each container is comprised of a (semi-)permeable membrane filter.

The term "bottom" as used herein is understood to indicate the lower part of the container or a position essentially near the base of the container, such as to provide the container with a certain volume above the membrane filter, but below the passageway or container dividing wall, if present, and includes the lower edge or base of the container wall.

In another preferred embodiment, the method involves the use of a microtiter plate particularly useful for distinctly detecting multiple analytes in one sample. For this embodiment, the individual containers in said microtiter plate are ordered in such a way, that two or more containers form a cluster of containers, based on the height of the walls that separate them, as measured from the bottom of the container, or based on the presence of a passageway connecting individual containers within a cluster (see FIG. 1 and 2).

The features of the walls separating the individual containers in a cluster of containers may be such that the walls separating two or more adjacent containers (container dividing walls) are lower than the walls separating two or more clusters of containers (cluster dividing walls). The workings of the microtiter plate according to such an embodiment of the invention are that when a sample fluid is applied to an arbitrary container in a first cluster of containers and the amount of sample fluid is such that the fluid level rises above the container dividing wall, at least a portion of said sample fluid will spill in the adjacent container. Thus, in principle, the height of the container dividing wall within a cluster is such that sample fluid may flow freely between adjacent containers within said first cluster when an volume of fluid larger than a certain critical volume is applied. However, fluid will not flow freely between two clusters, provided that the amount of said fluid is such that the fluid level does not rise above the cluster dividing wall.

In a second aspect, the present invention relates to a microtiter plate comprising a plurality of containers, wherein the bottom of each container comprises a (semi-)permeable membrane capable of directly or indirectly binding an analyte, and wherein each container is separated from an adjacent container by a container dividing wall, wherein the containers are grouped one or more in clusters, each cluster comprising at least two containers, wherein said clusters are separated from adjacent clusters by a cluster dividing wall and wherein at least part of the container dividing wall is lower than the cluster dividing wall or wherein the container dividing wall contains at least one passageway connecting at least two adjacent containers within a cluster, said passageway being at a distance from the bottom of the container and at least partly below the top of the container.

Within each cluster of containers, various analytes from one sample are preferably detected simultaneously, each analyte being preferably detected in a distinct container. As such, the membrane filter of various individual containers may be coated with different capture ligands, details of which will be described herein below.

In an alternative embodiment of a microtiter plate according to the present invention, the container walls and cluster walls need not differ in height but, instead, a passageway, for instance in the form of an indent or opening, bore or gate, is provided between individual containers within a cluster, but not between individual containers between clusters. Said passageway is essentially provided at a position in the container wall that is at some distance from the bottom of said container, such that a certain amount of fluid may be provided to the container without said fluid flowing or spilling to an adjacent and connected container. This features bears the advantage that individual containers may be provided with different reagents, that, in the case the reagents are provided in a volume of fluid that is lower than the spill-over volume of said container, will remain in one container without traversing to adjacent containers. In this way, the (semi-)permeable membranes in individual containers can be provided with different capture ligands in a simple manner.

The term "spill-over volume" as used herein, is understood to encompass the critical volume, above which the applied fluid starts to flow into an adjacent container within a cluster.

A microtiter plate according to the present invention does not only support a method of the invention wherein a single delivery action or application of a sample fluid to a container results in a partition of that sample over multiple containers, but also methods comprising single deliveries of washing fluids and single deliveries of detection media and reagents. In such a microtiter plate, fluids are automatically and instantly aliquoted over multiple containers, provided that the fluid volume provided by said delivery is at least the spill-over volume of an individual container times the number of containers in that cluster. This greatly reduces the number of deliveries necessary for performing the detection assay. It is preferred, therefore, that the spill-over volume of all containers on a microtiter plate is essentially equal.

In a particularly preferred embodiment of a microtiter plate according to the invention, each cluster of containers comprises at least 2, preferably at least $n^2$ adjacent containers, wherein n is an integer, preferably an integer from 2-10, more preferably 2-5. The maximum number of containers in a cluster will depend on the type of microtiter plate used (i.e. the total number of containers or wells provided thereon) and the number of clusters on said microtiter plate. In principle a microtiter plate may have one, but has preferably more clusters, each cluster preferably identical to the other.

Figure 1:
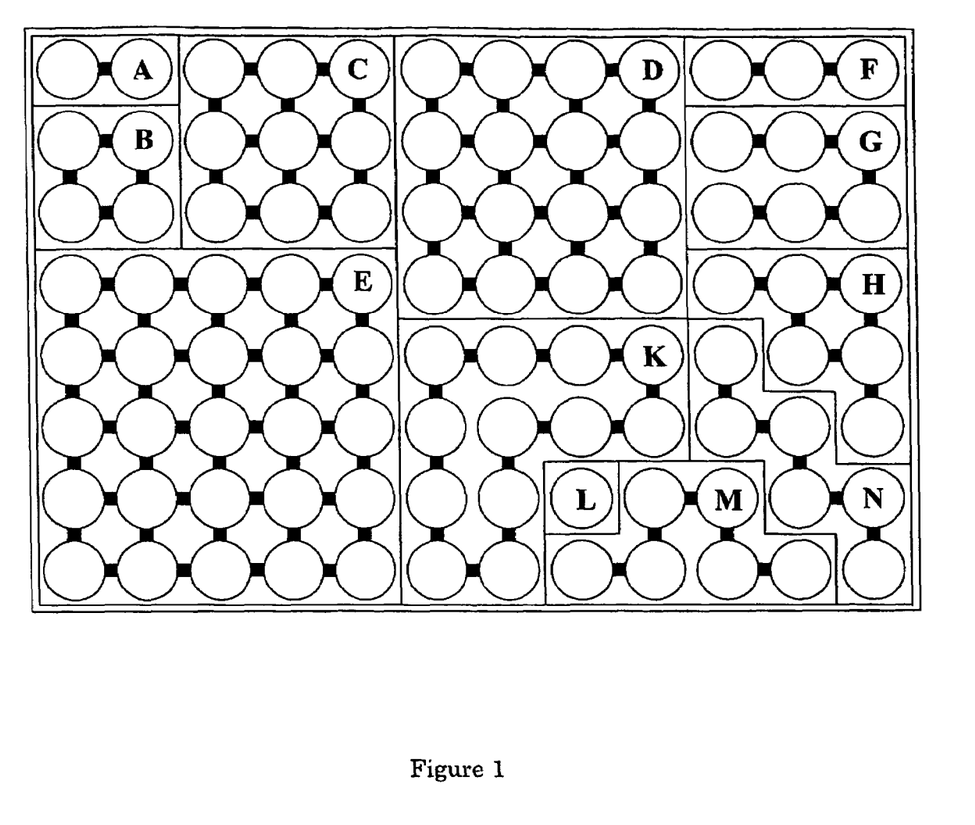
Figure 2:
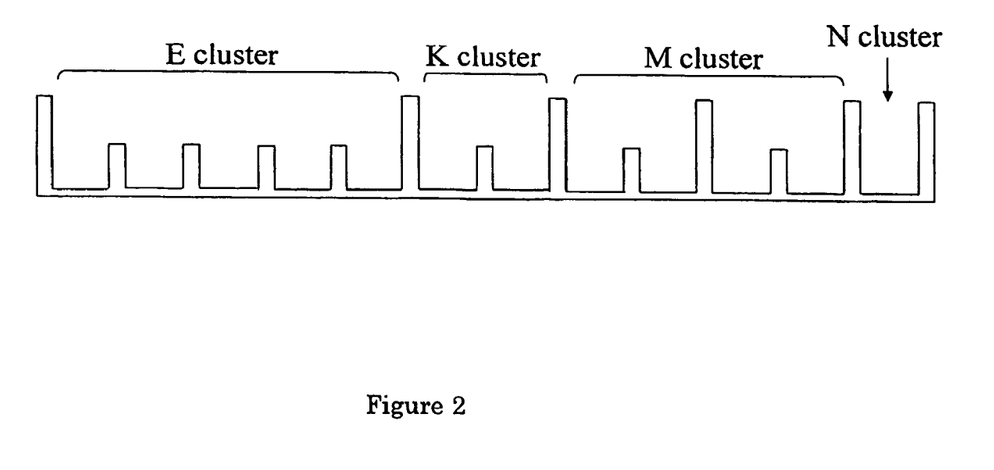

Each container within a cluster is not necessarily connected by spill-over to each and every adjacent container within that cluster. For instance, as can be seen in FIG. 1 and 2, clusters indicated by F, G, H, K, M and N, will also be completely and evenly filled with fluid when the volume thereof is at least the spill-over volume of an individual container times the number of containers in that cluster. The cluster can take any shape or form as defined by the interconnected containers comprising it, but square, rectangular of linear forms are preferred because they allow easier identification by marks on the plate.

A microtiter plate according to the present invention is preferably suitable for the detection of one analyte per container, and multiple analytes per cluster.

The arrangement of a microtiter plate according to the present invention may be such that one or more clusters, or preferably one or more containers within a cluster are devoted to internal standards, controls and calibrators. For example, one or more containers may be left without capture ligand or may be coated with a blocking agent to inhibit binding of the analyte to the membrane or with a biomaterial not expected to participate in a reaction with a sample; such containers may be used to measure and/or correct for non-specific binding of labels to the container surface. In another example, one or more containers are coated with a labeled reagent (e.g., a reagent labeled with an. detection label); such containers may be used to measure and/or correct for conditions that may affect the generation and measurement of signal from a label (e.g., pH, temperature, chemical interferents, colored species, etc.). In another example, one or more containers are used to carry out a control assay for a control analyte that is spiked into the assay mixture. Preferably, the control assay is similar in format to assays carried out in other containers of a cluster. Control assays may be used to measure and/or correct for non-specific binding, conditions that affect the generation of signal from a label and conditions that affect assay reactions (variations in incubation time, temperature, mixing, etc.).

A method to detect multiple analytes in one sample is now particularly well supported by such a clustered ordering of the containers within the microtiter plate of the invention. It is required in a microtiter plate of the invention that walls of at least a certain height remain between adjacent containers, or that a passageway is at some distance from the bottom. The result thereof being that within a cluster of adjacent containers, each individual container may be provided with a fluid comprising a different specific capture ligand, so that membrane filters in different containers are provided with different specific capture ligands, as a result whereof different specific analytes from a sample may be captured or immobilized by indirect binding to the membrane filter on the bottom of individual containers. Detections for different analytes from one individual sample may be carried out simultaneously in those adjacent containers. A microtiter plate of the present invention comprises in one embodiment at least one container in a cluster of containers that comprises a capture ligand for binding an analyte to the membrane filter of said container. In another embodiment each container in a cluster of containers comprises a different capture ligand for indirectly binding the analyte to the membrane filter.

In case various containers in one cluster are provided with different (preferably known, most preferably calibrated) amounts of capture ligands, such that different (preferably known, most preferably calibrated) amounts of analyte are bound in different containers within a cluster, such a cluster may be used to determine the amount of analyte present in the sample, or determine the binding capacity of the capture ligand.

The specific capture ligands immobilized to the membrane filters of individual containers may for instance be selected from specific antibodies to infectious disease agents or selected structures or parts from infecting agents such as described above. The skilled person will understand that many different capture ligands to analytes may be selected to bind analytes to membrane filters of specific containers. Furthermore, the skilled person will understand that the detection procedure may be selected from many different binding assay formats and that such a procedure may even be performed with non-specific antibodies in case the capture to the membrane filter itself is specific, although the use of specific antibodies is preferred.

In order to produce a microtiter plate that is particularly useful for distinctly detecting multiple analytes in one sample according to a method of the invention, the skilled person will understand that the walls of adjacent containers in a standard microtiter plate may be reduced in height or (partially) removed by milling away (part of) the walls separating two or more adjacent containers. Alternatively, for instance, a microtiter plate comprising 96 square bottomless containers may be glued on top of a microtiter plate of 384 square containers the base of which is provided with a (semi-)permeable membrane filter. The alignment of the wells of the top plate relative to the lower plate should be such that the bottom corner of each wall of a container of the 96 bottomless wells plate lines up with 4 containers in the lower plate. By such a procedure, a microtiter plate according to the present invention comprising 96 clusters, each cluster comprising 4 containers is provided. Also passageways as described above may be drilled or provided in other manners to adjacent containers within a cluster such that all containers in that cluster are connected in some way, either directly or indirectly.

In a final aspect, the present invention relates to the use of a microtiter plate according to the invention for the detection of analytes in a sample. In a preferred use, multiple, different analytes are detected on said plate simultaneously. The use according to this aspect of the invention may be advantageous for all fields of chemical and (bio)medical analysis wherein samples must be subjected to multiple binding assays. Preferably, the use relates to the diagnosis of multiple disease agents.

In a particularly preferred embodiment of various aspects of the present invention a multiple analyte assay is provided which assay comprises the use of a microtiter plate according to the present invention wherein in each cluster of containers, various analytes from one sample are detected simultaneously, each analyte preferably being detected in a separate container. As stated, this may very suitable be achieved by coating the membrane filter of various individual containers with different capture ligands.

In a most preferred embodiment, the various capture ligands are chosen such that the microtiter plate of the present invention supports the performance of specific diagnostic menus or panels as described above that, for instance, when performed, indicate the specific causative agent of a disease. For instance, menus aimed at diagnosing the causative agent of mastitis may then be performed by using a microtiter plate of the present invention of which the membrane filter of the individual containers is coated with capture ligands that are capable of specifically binding the causative agents of mastitis, e.g. *Escherichia coli, Staphylococcus. aureus, Streptococcus uteris, Streptococcus galacticae* and/or *Streptococcus agalacticae,* potentially present in a suspected sample. Alternatively, or in combination therewith, antibodies against such agents that are produced by the subject from which the sample is obtained may be detected in said sample.

Other suitable such menus include menus for specific disease agents or for specific disease types such as:

Pestiviruses (including capture ligands for Bovine Viral Diarrhea Virus (BVDV), Border Disease Virus (BDV), Classical Swine Fever Virus (CSFV), etc. and/or antibodies thereto)

Diarrhea (including capture ligands for *E. Coil*, Rotavirus, Coronavirus (e.g. coronavirus (BCV)), *Cryptosporidium,* enterotoxigenic *Escherichia coli* K99, *Salmonellae* spp. and/or antibodies thereto)

Respiratory diseases (including capture ligands for bovine herpes Virus 1 (BHV1), BVDV, bovine respiratory syncytical virus (BRSV), bovine parainfluenza-3 virus (PI-3), adenovirus, *Mycoplasma bovine, Pasteurella haemotytica* and/or antibodies thereto)

Johne's disease (increased sensitivity): (including e.g. capture ligands for antibodies against *Mycobacterium paratuberculosis,* gamma interferon, etc.)

Aberrant prion menu (including capture ligands for nvBovine spongiform encephalopathy (nvBSE), nvScrapie, nvCWD, nvCFJ)

Alternatively, a microtiter plate of the present invention may be designed such that it supports the performance of specific diagnostic menus relating to a particular animal, for instance comprising capture ligands for various causative agents or for antibodies produced there against in pigs, sheep, cows, horses, etc. For instance:

Cows (cattle): A menu for which may include capture ligands for detecting the presence of Bovine Respiratory Syncytial Virus (BRSV); Bovine Viral Diarrhoea Virus (BVDV); *Brucella,* optionally subdivided in *B. abortus* and *B. melitensis;* Foot and Mouth Disease virus (FMDV); Leptospirosis (e.g. Leptospira interrogans serovar hardjo); *Dictyocaulus viviparous* (lungworm); BSE (mad cow disease); *Hemophilus somnus; Pasteurella haemotytica;*

Pigs: A menu for which may include capture ligands for detecting the presence of Classical Swine Fever virus (CSFv), optionally strain specific; Foot and Mouth Disease virus (FMDV); Porcine Parvo Virus (PPV); Pseudorabies virus; Swine Vesicular Disease virus (SVDV), porcine respiratory and reproductive syndrome virus (PRRSV or Lelystadvirus), porcine circovirus 1 and 2 (causative of multisystemic wasting syndrome (PMWS)), Swine Influenza Virus (SIV).

Sheep: A menu for which may include capture ligands for detecting the presence of *Brucella*, optionally subdivided in *B. abortus* and *B. melitensis;* Foot and Mouth Disease virus (FMDV)

Also various purpose-specific menus may be designed such as export specific menus that are country-dependent, such as menus comprising capture ligands to perform e.g. an Aujeszky-test, a Salmonella test, an SVDV-test and a fourth test, which may be varied depending on the specific status of the various diseases in that country.

Another purpose specific menu may for instance comprise a blood bank specific menu comprising a capture ligand menu for detection of the various infectious disease agents that are tested for in blood donation facilities, e.g. binding partners for human immunodeficiency viruses (HIV) 1 and 2; hepatitis B virus (HBV); Hepatitis B core Antibody (AHBC); hepatitis C virus (HCV); human T-lymphotropic viruses (HTLV) I and II; syphilis; gonorrhea; Lyme disease and Creutzfeldt-Jakob Disease (CJD).

Yet other menus may for instance include such menus for specific allergy testing.

The invention claimed is:

1. A microtiter plate comprising a plurality of wells of a rigid material selected from the group consisting of glass, polystyrene, polyacryl, polyamide, polyethylene, polypropylene, acrylate butadiene styrene (ABS), polyvinylchloride (PVC), nylon ethylene-vinyl acetate (EVA) polyethylene terephthalate (PET), and combinations thereof, wherein each well is a well of a regular microtiter plate wherein, each well is separated from an adjacent well by a well-dividing wall, wherein the bottom of each well is comprised of a (semi-)permeable membrane filter capable of directly or indirectly binding an analyte, wherein the wells are grouped in one or more clusters, each cluster comprising at least two wells wherein said clusters are separated from adjacent clusters by a cluster dividing wall and wherein at least part of the well dividing wall is lower than the cluster dividing wall or wherein the well dividing wall contains at least one passageway connecting at least two adjacent wells within a cluster, said passageway being at a distance from the bottom of the well and at least partly below the top of the well.

2. Microtiter plate according to claim 1, wherein each cluster of containers comprises at least $n^2$ containers, wherein n is an integer.

3. The microtiter plate according to claim 2, wherein n is an integer of from 2 to 10.

4. The microtiter plate according to claim 2, wherein n is an integer of from 2 to 10.

5. Microtiter plate according to claim 1, wherein said membrane filter comprises polyvinyldene fluoride (PVDF).

6. Microtiter plate according to claim 1, wherein at least one well in a cluster of wells comprises a capture ligand for specifically binding an analyte to the membrane filter of said well.

7. Microtiter plate according to claim 4, wherein said analyte is an infectious disease agent or an antibody there against.

8. Microtiter plate according to claim 1, wherein at least two wells in a cluster of wells comprise a different amount of capture ligand for specifically binding an analyte to said membrane filter.

9. Microtiter plate according to of claim 1, wherein at least two wells in a cluster of wells comprise a different capture ligand for specifically binding an analyte to said membrane filter.

10. Microtiter plate according to claim 1, wherein at least one cluster comprises capture ligands specific for the detection of the causative agent of scrapie, bovine spongiform encephalopathy (BSE); chronic wasting disease and/or Creutzfeldt-Jakob disease.

11. Microtiter plate according to claim 10, wherein at least one cluster comprises capture ligands for the detection of prions $PrP^{Sc}$, $PrP^{BSE}$, $PrP^{CWD}$ and/or $PrP^{CJD}$.

12. A method for the detection of one or more analytes in a liquid sample comprising:
   a) providing a microtiter plate according to claim 1;
   b) applying said liquid sample to at least one cluster of wells, filtering said sample through said membrane filter, thereby binding said one or more analytes to said membrane filter or capture ligand, and optionally performing washing steps; and
   c) detecting said bound one or more analytes in said wells by performing a binding assay on said membrane filter.

13. Method according to claim 12, wherein said one or more analytes comprise an infectious disease agent or an antibody there against.

14. Method according to claim 13, wherein the infectious disease agent is a prion.

15. Method according to claim 14, wherein the prion is a prion causing bovine spongiform encephalopathy.

16. Method according to claim 12, wherein the binder assay is a chemiluminescent immunoassay.

* * * * *

UNITED STATES PATENT AND TRADEMARK OFFICE
CERTIFICATE OF CORRECTION

| | | |
|---|---|---|
| PATENT NO. | : 7,618,829 B2 | Page 1 of 1 |
| APPLICATION NO. | : 10/568633 | |
| DATED | : November 17, 2009 | |
| INVENTOR(S) | : Keizer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 346 days.

Signed and Sealed this

Twenty-sixth Day of October, 2010

David J. Kappos
*Director of the United States Patent and Trademark Office*